United States Patent [19]

Shen et al.

[11] Patent Number: 5,446,118
[45] Date of Patent: Aug. 29, 1995

[54] FLUORINATED ACRYLIC MONOMERS CONTAINING URETHANE GROUPS AND THEIR POLYMERS

[75] Inventors: Ya X. Shen; Robert Thompson, both of Wilmington, Del.

[73] Assignee: W. L. Gore & Associates, Inc., Newark, Del.

[21] Appl. No.: 310,823

[22] Filed: Sep. 22, 1994

Related U.S. Application Data

[63] Continuation-in-part of Ser. No. 289,159, Aug. 11, 1994, abandoned.

[51] Int. Cl.$^6$ .................. C08F 18/20; C07C 261/00
[52] U.S. Cl. ........................... 526/245; 560/26
[58] Field of Search ................ 560/26; 526/245

[56] References Cited

U.S. PATENT DOCUMENTS

| | | |
|---|---|---|
| 4,117,199 | 9/1978 | Gotoh et al. . |
| 4,290,970 | 9/1981 | Merger et al. . |
| 4,384,040 | 5/1983 | von Meer . |
| 4,547,322 | 10/1985 | Fukuoka et al. . |
| 4,683,877 | 8/1987 | Ersfeld et al. . |
| 4,835,300 | 5/1989 | Fukui et al. . |
| 4,898,849 | 2/1990 | Kang . |
| 4,920,190 | 4/1990 | Lina et al. ............ 560/26 |
| 4,989,593 | 2/1991 | Campagna et al. . |
| 4,994,112 | 2/1991 | Majewicz et al. . |
| 5,016,622 | 5/1991 | Norvell . |
| 5,027,803 | 7/1991 | Scholz et al. . |
| 5,144,056 | 9/1992 | Lina et al. . |
| 5,286,279 | 2/1994 | Wu . |

FOREIGN PATENT DOCUMENTS

| | | | |
|---|---|---|---|
| 0225826 | 6/1987 | France ................ 560/26 |
| 3330947 | 3/1985 | Germany ............ 560/26 |
| 2100722 | 1/1983 | United Kingdom ........ 560/26 |

OTHER PUBLICATIONS

Patent Abstract of Japan—vol. 6, No. 7 (C-87) (885) 16 Jan. 1982—JPA 56131687 (Asahi Glass K.K.)—15 Oct. 1981.

*Primary Examiner*—Joseph L. Schofer
*Assistant Examiner*—N. Sarofim
*Attorney, Agent, or Firm*—Gary A. Samuels

[57] ABSTRACT

A composition of the formula:

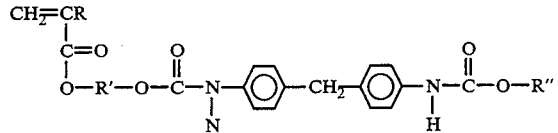

is disclosed. Polymers of the composition are useful to coat onto substrates to impart oil and water repellency.

6 Claims, 1 Drawing Sheet

FLUORINATED ACRYLIC MONOMERS CONTAINING URETHANE GROUPS AND THEIR POLYMERS

CROSS-REFERENCE TO RELATED APPLICATIONS

This application is a continuation-in-part of application Ser. No. 08/289,159 filed Aug. 11, 1994, now abandoned.

FIELD OF THE INVENTION

This invention relates to acrylic monomers which contain urethane units and perfluorinated alkyl groups; and to their polymers, including copolymers; and to substrates coated with the polymer.

BACKGROUND OF THE INVENTION

Compounds and polymers having perfluorinated side chains are known to have oil and water repellant properties. One such class of compounds that are precursors for such polymers are fluorinated acrylic resins.

Fluorinated acrylic resins are known and are available commercially. For example, perfluoroalkyl acrylates, $CH_2=CH-COO-CH_2CH_2(CF_2)_nF$, are available as Zonyl TA-N from the DuPont Company.

Fluorinated acrylic resins which contain urethane units are also known, as seen by Lina, et al. U.S. Pat. No. 5,744,056. These resins can be applied to a number of substrates to provide coatings or to be imbibed into the substrate in order make use of the resins as protective coatings.

However, the water and oil repellancy of such perfluorinated alkyl acrylic resins can be improved. The pendant perfluoro alkyl side chains on the acrylic polymers have proven to be difficult to orient in a configuration best suited to provide water and oil repellancy.

SUMMARY OF THE INVENTION

It has been discovered that to provide optimum water and oil repellancy the pendant perfluorinated alkyl groups should be long chained, and should be permanently aligned parallel to adjacent pendant groups attached to adjacent acrylic backbone units. Thus a coated substrate will present a surface protected by an array of pendant perfluoroalkyl groups so as to maximize water and oil repellancy.

In this invention, the pendant perfluoroalkyl groups are modified by the presence of urethane groups intermediate the acrylic backbone and the perfluorinated groups. The affinity of the urethane groups for one another keeps the entire pendant chain substantially in fixed alignment even when subjected to adverse conditions such as heat.

The monomers of the invention are represented by the formula:

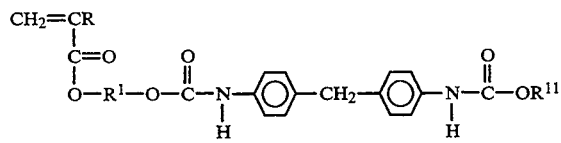

wherein R is H or $-CH_3$; $R^1$ is alkyl of 2-8 carbons; and $R^{11}$ is fluorinated alkyl of 8-20 carbons.

Preferably $R^{11}$ is alkyl perfluoroalkyl $(CH_2)_n R_f$ where n is 1 or 2 and $R_f$ is perfluorinated alkyl of 6-14 carbons).

In a more limited embodiment, inventive monomers can be represented by the formula:

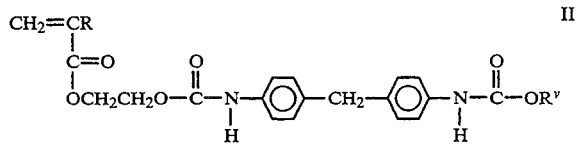

where R is H or $CH_3$; $R^v$ is $-CH_2CH_2(CF_2)_n F$ or $-CH_2(CF_2)_n F$ and n is a cardinal number of 6-14.

The polymers of the invention include homopolymers and copolymers of the monomers of the invention. The effect of these monomers in forming polymers with fixed side chains, i.e., side chains fixed into a set pattern can be seen in FIG. 1 where the affinity of the —NH-COO— urethane groups is self evident.

Also included in the invention are substrates coated with the polymers of the invention.

DETAILED DESCRIPTION OF THE INVENTION

Figure 1:
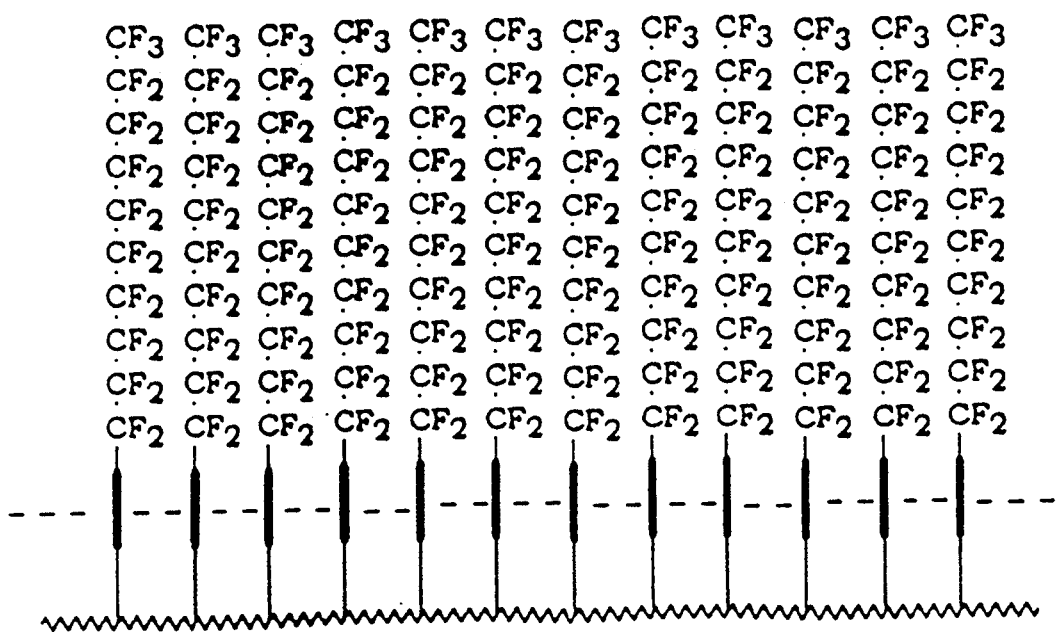
FIG. 1 is a molecular model of a polymer of the invention.

Referring to FIG. 1, the symbol  represents the —$CH_2$—CR— backbone of the polymer formed from the monomer of the invention; the symbol represents the urethane linkage; and the—lines between these linkages represents molecular attraction between the urethane linkages. It is this attraction that greatly enhances the bonding, or "fixing," potential of applicants polymers over the polymers of U.S. Pat. No. 5,144,056.

The monomers of the invention can be prepared by first reacting a perfluoroalkyl alcohol, e.g., $$HO-CH_2CH_2(CF_2)_n F \qquad III$$

where n is a cardinal number of 6-14, which are available commercially, with 4,4' diphenyl methane diisocyonate (MDI). An excess of MDI is employed in order to enhance formation of the mono-urethane adduct product

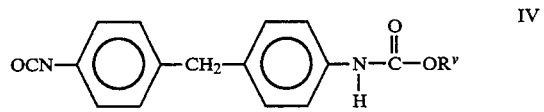

Then the adduct IV is reacted with w-hydroxyalkyl acrylate, preferably 2-hydroxyethyl acrylate. A slight excess is used to facilitate reaction of all the —NCO groups of adduct IV. Thus the monomer of formula I of the invention is formed.

The first step of synthesizing monomer I, preparation of intermediate IV, is carried out at elevated temperatures under an inert atmosphere, e.g., anhydrous nitrogen, as isocyanate groups are moisture sensitive, and in an organic hydrocarbon solvent, such as toluene. The intermediate IV is purified by recrystallization. The second step, which is the reaction of IV with 2-hydroxyalkyl acrylate, is also carried out under an inert atmosphere and an organic solvent, usually anhydrous tetrahydrofuron (THF) at reflux. In order to ensure a 100% yield, a small excess of 2-hydroxyalkyl acrylate may be used. The unreacted 2-hydroxyalkyl acrylate can be removed by water extraction or reprecipitation of monomer I in water.

Monomer I can be homopolymerized or copolymerized with other copolymerizable comonomers in proportions of about 1 to 90 percent by weight, preferably 50–90 percent, of monomer I.

Examples of comonomers include lower olefinic hydrocarbons, halogenated or otherwise, such as ethylene, propylene, isobutene, 3-chloro-1-isobutene, butadiene, isoprene, chloro- and dichlorobutadienes, fluoro- and difluorobutadienes, 2,5-dimethyl-1,5-hexadiene, diisobutylene; vinyl, allyl or vinylidene halides, such as vinyl chloride or vinylidene chloride, vinyl fluoride or vinylidene fluoride, allyl bromide, methallyl chloride;

styrene and its derivatives, such a vinyltoluene, x-methylstyrene, x-cyanomethylstyrene, divinylbenzene, N-vinylcarbazole; vinyl esters such as vinyl acetate, vinyl propionate, the vinyl esters of the acids known commercially by the name "Versatic acids," vinyl isobutyrate, vinyl succinate, vinyl isodecanoate, vinyl stearate, divinyl carbonate; allyl esters such a allyl acetate and allyl heptanoate; alkyl vinyl or alkyl allyl ethers, halogenated or otherwise, such a cetyl vinyl ether, dodecyl vinyl ether, isobutyl vinyl ether, ethyl vinyl ether, 2-chloroethyl vinyl ether, tetra allyloxyethane, vinyl alkyl ketones such a vinyl methyl ketone, unsaturated acids, for example acrylic, methacrylic, a-chloroacrylic, crotonic, maleic, fumaric, itaconic, citraconic and senecioic acids, their anhydrides and their esters such as vinyl, allyl, methyl, butyl, isobutyl, hexyl, heptyl ethyl-2-hexyl, cyclohexyl, lauryl, stearyl and 1-alkoxyethyl acrylates and methacrylates, dimethyl maleate, ethyl crotonate, acid methyl maleate, acid butyl itaconate, glycol or polyalkylene glycol diacrylates and dimethacrylates, such as ethylene glycol or triethylene glycol dimethacrylate, dichlorophosphatoalkyl acrylates and methacrylates such as di-chlorophosphatoethyl methacrylate, and also acid bis(methacryloyloxyethyl) phosphate and methacryloyloxpropyltrimethoxysilane; acrylonitrile, methacrylonitrile, 2-chloroacrylonitrile, 2-cyano-ethyl acrylate, methyleneglutaronitrile, vinylidene cyanide, alkyl cyanoacrylates such a isopropyl cyanoacrylate, trisacryloylhexahydro-s-triazine, vinyl-tri-chlorosilane, vinyltrimethoxysilane, vinyltriethoxyilane, N-vinyl-2-pyrrolidone; allyl alcohol, allyl glycolate, isobutenediol, allyloxyethanol, o-allylphenyl, divinylcarbinol, glycerol allyl ether, arylamide, methacrylamide, maleamide and maleimide, N-(cyanoethyl)acrylamide, N-isopropylacrylamide, diacetoneacrylamide, N-(hydroxymethyl-)acrylamide and methacrylamide, N-(alkoxymethly-)acrylamides and methacrylamides, glyoxal bisacryl-amide, sodium acrylate or methacrylate, 2-sulphoethyl acrylate, vinylsulphonic and styrene-p-sulphonic acids and their alkali metal salts, 3-amino-crotono- nitrile, monoallyl amine, vinylpyridines, glycidyl acrylate or methacrylate, allyl glycidyl ether, acrolein, N,N-dimethylaminoethyl or N-tert-butylamino ethyl methacrylate; the unsaturated fluorine esters of the general formula:

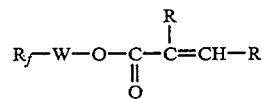

in which $R_f$ is perfluoralkyl of 2–20 carbons, R is H or methyl and W is a divalent linking moiety.

Among the above-mentioned comonomers, more special preference is given to simple alkyl acrylates and methacrylates or those containing a hydroxyl, amino or sulphonic acid functional group, methacrylates of polyethylene glycol ethers, vinyl ethers, vinyl or vinylidene chloride and fluoride, vinyl pyrrolidone, acrylamide and its derivatives, and acrylic or methacrylic acid.

The fluorinated polymers of the invention can be prepared by polymerization in an organic solvent or in an aqueous emulsion, at a temperature which can range from room temperature to the boiling point of the reaction medium, but preferably at between 70° and 100° C.

The polymerization in a solvent medium can be carried out in ketonic solvents (for example acetone, methyl ethyl ketone, methyl isobutyl ketone), alcohols (for example isopropanol), esters (for example ethyl acetate or butyl acetate), ethers (for example diisopropyl ether, ethylene glycol ethyl or methyl ether, tetrahydrofuran, dioxane), aliphatic or aromatic hydrocarbons, halogenated hydrocarbons (for example perchloroethylene, 1,1,1-trichloroethane, trichlorotrifluoroethane), dimethylformamdie or N-methyl-2 pyrrolidone.

The polymerization is performed in the presence of one or more initiators, which can be used in the proportion of about 0.1 to 1.5% relative to the total weight of the monomers involved. As initiators, peroxides can be used, such as, for example, benzoyl peroxide, lauryl peroxide, succinyl peroxide and tert-butyl perpivalate, or azo compounds such as, for example, 2,2,-azobisisobutyronitrile, 4,4,-azobis(4-cyanopentanoic acid) and azodicarbonamide. It is also possible to polymerize in the presence of UV radiation and photoinitiators such as benzophenone, 2-methylanthraquinone or 2 chlorothioxanthone. The length of the polymeric chains can, if so desired, be adjusted by means of chain transfer agents such as alkyl mercaptans, carbon tetrachloride or triphenylmethane, used in the proportion of 0.05 to 0.5% relative to the total weight of monomers.

The polymerization in aqueous emulsion can be carried out according to well-known techniques, in discontinuous or continuous fashion. The surfactants used for the emulsification can be cationic, anionic or nonionic, according to the ionic nature desired for the final dispersion, and are preferably chosen from the best oil-in-water emulsifiers which are as little wetting as possible. Cationic/nonionic or anionic/nonionic surfactant systems are preferably used. As examples of surfactants which can be used, the following may be mentioned more especially: in the cationic series, long-chain tertiary amine salts such as N,N-dimethyloctadecylamine acetate, and the quaternary ammonium salts of fatty amines such as trimethylcetylammonium bromide or trimethyldodecylammonium chloride; in the anionic series, alkali metal salts of long-chain alkylsulphonic aids and alkali metal arylalkyl sulphonates; in the nonionic series, condensation products of ethylene oxide with fatty alcohols or with alkyl phenols.

It can also be advantageous to use surfactants having a perfluorinated hydrophobic chain, such as, for example, ammonium perfluorooctanoate or potassium N-perfluorooctylsulphonyl-N-ethylaminoacetate.

To facilitate the emulsification of the monomers, it is generally necessary to use organic solvents such as, for example, ketones (acetone, methyl ethyl ketone, methyl isobutyl ketone), glycols or ethylene glycol ethers, alcohols (methanol, ethanol, isopropanol), or mixtures of these solvents. The amount of solvent should not generally exceed the total weight of the monomers.

As initiators of polymerization in aqueous emulsion, it is possible to use water-soluble products, such as inorganic peroxides (for example hydrogen peroxide) and persalts (for example potassium persulphate), or initiators which are insoluble in water such as organic peroxides and the azo compounds mentioned above.

Regardless of the method by which they are obtained, the fluorinated polymers according to the invention can optionally be isolated according to known methods, such as, for example, precipitation or evaporation of the solvent.

The fluorinated polymers according to the invention are excellent hydrophobic and oleophobic agents on very diverse substrate materials such as paper, nonwoven articles, textiles based on natural, artificial or synthetic fibers, plastics, wood, metals, glass, stone and cement. They are especially useful for the protection of fabrics or paper or cast liners for mending bones. For example, in a cast liner made of padding provided with a protective layer of liquid water-impermeable, water vapor-permeable material, such as stretched porous polytetrafluoroethylene, the padding can be treated with the fluorinated polymers of the invention. The material can be on one or on both sides of the padding, but preferably is only on one side. Furthermore, the material, when made of a membrane of stretched porous polytetrafluoroethylene can itself be coated with a hydrophilic layer that transports water by an absorption-evaporation mechanism, but which does not allow passage of air. Representative cast liners of this type are described in U.S. Pat. No. 5,016,622 to Norvell, incorporated herein by reference.

The fluorinated polymers are also useful where enhanced hydrophobic or oleophobic properties are desired, such as on paper products, such as photocopy paper, cardboard boxes, wall paper, wall board, paper bags, paper filters, billboard paper. In general, where any paper needs to be protected, the polymers are useful. Additional paper products for coating include baseball cards, blueprint paper, cook book paper, wrapping paper for fast foods, file cards for recipe files, score cards (golf, baseball & other sporting events), instructions for items for things normally assembled outside, lab notebook paper, legal documents, licenses (fishing, hunting, etc.), maps, menus, notebook paper for outdoor use, outdoor poster paper, paperbacks, sold at the shore, parking tickets, practical joke items, table cloths, tags for outdoor use, text books for children, water/board safety books, wrapping paper, and the like.

For application to substrates, the solutions of polymers are generally diluted with a solvent identical to or compatible with that used for the polymerization; while the emulsions of polymers are diluted with water. The application of the solutions or emulsions can be carried out according to a number of techniques, such as spraying, brush-coating, padding, or the like. Depending on their nature, the substrates treated can be dried at room temperature or at temperatures which can range up to 200° C.

The amount of polymer to be employed can vary within wide limits, depending on the nature of the substrate and the fluorine content of the polymer. On leather, this amount is generally within the range of about 1 to 10 g/m$^2$.

The examples which follow, in which the parts and percentages are understood to be by weight, except where otherwise stated, illustrate the invention without limiting it.

EXAMPLES

In addition to the monomers and polymers described above, the following compounds and polymers were also synthesized for comparison studies; 2-acryloxylethyl 1H,1H-perfluorooctyl methylenedi-p phenyl dicarbamate (V); 1H,1H-perfluorooctyl methylenedi-p-phenyl dicarbamate (VI); and poly(2-perfluoroalkylethyl acrylate) (VII). These compositions have the following formulas:

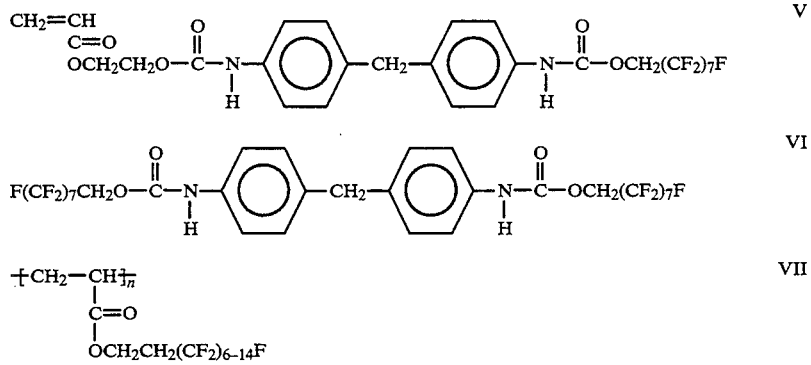

Perfluoroalkyl acrylate (Zonyl TA-N) and perfluoroalkyl alcohol (Zonyl BA-N) were obtained from the E. I. DuPont de Nemours and Company, Inc. and used without further purification. Azobis(2-methylpropionitrile) (AIBN) (99%) was purchased from Alfa Products. Diphenyl methane diisocyanate (MDI) was obtained from Mobay Chemical and stored in an oven at 40° C. to precipitate any dimer before using. 2-Hydroxylethyl acrylate (97%) from Polysciences, Inc. were used as obtained. 1H, 1H-perfluorooctanol and fluorinated solvents were obtained from PCR Co. Anhydrous toluene was obtained from Aldrich Chemicals.

Proton NMR analysis was done on a 360 MHz NMR Spectrometer by Spectra Data Service, Champaign, Ill. HPLC, DSC and DCA analyses were carried out on HP-1090, TA-DSC-2910 and Cahn CDA322, respectively.

Their weight percentages are 30% (VI), 40% (V) and 30% (believed to be (VIII)).

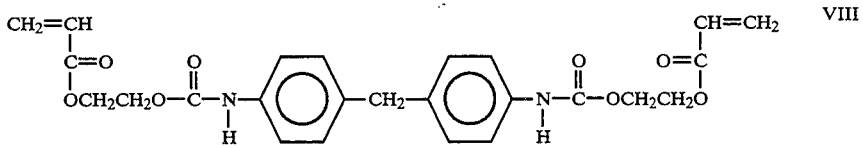

EXAMPLE 1

Synthesis of Bis(2-acryloxyl-2'-perfluoroalkyl)ethyl methylenedi-p-phenyl dicarbamate (Formula II)

MDI (82.8 g, 0.331 mol) was charged into a 500 ml, 3 necked dry round bottom flask equipped with a condenser, a magnetic stirrer, nitrogen flow system and a heating mantle. Anhydrous toluene (150 ml) was added and the solution was heated to reflux under anhydrous nitrogen. Perfluoroalkyl alcohol (Zonyl BA-N) (34.0 g, 0.066 mol) was added dropwise over 30 minutes. The solution was then refluxed under nitrogen overnight.

Heat was removed. White crystalline solid was observed when the solution was cooled down to room temperature. In 5 hours time at room temperature, the solid was filtered and recrystallized twice in anhydrous toluene under nitrogen and then vacuum dried overnight at room temperature. About 35.0 grams of white crystalline solid was obtained (some product was lost during recrystallization). The solid showed one major spot on thin layer chromatography (TLC) with another trace above the major spot. This solid product is intermediate IV.

The intermediate IV (23.0 g, 0.03009 mol) was charged into a 250 ml, 3 necked round bottom flask equipped as above. Anhydrous tetrahydrofuran (THF) (100 ml) was added with 2 drops of Metacure T-12 catalyst (Air Products and Chemical, Inc.). 2-Hydroxylethyl acrylate (5.00 g, 0.04306 mol) was added slowly with a syringe. The solution was refluxed under nitrogen with magnetical stirring for 3 hours.

The solution was poured into 800 ml of distilled water with stirring in a beaker. The white precipitate was filtered, vacuum dried overnight at room temperature and weighted 25.9 g.

EXAMPLE 2

Equal molar of MDI was reacted with 1H, 1H-perfluorooctanol in anhydrous THF through controlled reaction, i.e. adding 1H, 1H-perfluorooctanol/THF solution to MDI/THF solution very slowly using a syringe pump. Kinetic control of the reaction maximized the yield of intermediate IV.

After the reaction, 2-hydroxylethyl acrylate (1 eq. of total hydroxyl to isocyanate) was added into the flask to form a product mixture.

After removal of solvent, the mixture showed three spots on TLC, indicating that there were three major components in the mixture. The first two components were isolated and purified by column chromatography and recrystallization. Proton NMR analysis and melting point measurements evidenced that the first component was compound VI and the second one was compound V. The third component which was not purified was believed to be bis(2,2'-acryloxy)ethyl methylenedi-p-phenyl dicarbamate which structure is shown as VIII. The mixture was also quantitatively analyzed by HPLC. As expected, the HPLC trace had three peaks.

EXAMPLE 3

Excess MDI was reacted with 1H, 1H, 2H, 2H-perfluoroalkyl alcohol (Zonyl) BA-N) (molar ratio of MDI to the alcohol was 5 to 1) in anhydrous toluene by slow addition to Zonyl BA-N to MDI. The intermediate IV was isolated by recrystallization in anhydrous toluene under nitrogen once and then reacted with 2-hydroxylethyl acrylate to form a product mixture.

After removal of solvent, the mixture showed one major spot on TLC and two trace ones, indicating that there were three components in the mixture but their relative amounts are different than those in Example 3. HPLC analysis also proved that there were three components in the mixture and their weight percentages were 8% (VI analog), 90% (II) and 2% (believed to be VIII).

EXAMPLE 4

Preparation of Homopolymer of Monomer II

The monomer made in Example 1 (10.17 g, 0.01160 mol) was charged into a 100 ml, 3 necked round bottom flask equipped with a condenser, magnetic stirrer, nitrogen flow system and a temperature controlled oil bath heating system. Anhydrous 1, 4-dioxane (15 ml) was added with a syringe. The mixture was stirred at 90° C. with nitrogen bubbled through the solution for 10 minutes. Into the homogeneous solution, AIBN (0.003800 g) in anhydrous 1, 4-dioxane (2 ml) was added with a syringe. The solution was then stirred at 90° C. under nitrogen for overnight.

The polymer formed was precipitated into 600 ml of methanol, filtered and vacuum dried overnight.

EXAMPLE 5

Preparation of Copolymer Containing Monomer II

The monomer made in Example 1 (4.670 g, 0.005300 mol) and n-lauryl acrylate (4.670 g, 0.01943 mol) were charged into a 100 ml, 3 necked round bottom flask equipped same as that in Example 4. Anhydrous 1, 4-Dioxane (15 ml) was syringed into the flask and temperature of the oil bath was raised to 100° C. The homogeneous solution was bubbled with nitrogen for 10 minutes and then under nitrogen. AIBN (0.008110 g) in 1.5 ml of the 1, 4-dioxane was syringed into the flask. Viscosity increase was observed in 30 minutes. The solution was then stirred at 100° C. under nitrogen for overnight.

The polymer was precipitated into 800 ml of methanol, filtered and vacuum dried overnight.

This polymerization was also carried out in 1, 3-bistrifluoromethyl benzene (HFX).

EXAMPLE 6

Preparation of Copolymer Containing Monomer II

The monomer made in Example 1 (5.52 g, 0.006270 mol) and n-lauryl acrylate (1.950 g, 0.008100 mol) were charged into a 50 ml, 1 necked round bottom flask equipped same as that in Example 4. HFX (20 ml) was added with a syringe. Temperature of the oil bath was raised to 110° C. The solution was bubbled with nitrogen for 10 minutes and then under it. AIBN in 2 ml of HFX was syringed into the flask. The solution was stirred at 110° C. under nitrogen for overnight.

The polymer was precipitated into 800 ml of methanol, filtered and vacuum dried overnight.

This polymerization was also carried in DMF.

Comparative Example 1

Preparation of Zonyl TA-N Homopolymer 1H, 1H, 2H,2H-Perfluoroalkyl acrylate (Zonyl TA-N) (82.4 g, 0.145 mol) was charged into a 250 ml, 3 necked round bottom flask equipped the same as that in Example 5. 100 ml of PF-5070 was added. Temperature of the oil bath was raised to reflux and meanwhile the solution was bubbled with nitrogen for 10 minutes. Into the flask, AIBN 0.0475 g, 0.000290 mol) in 10 ml of HFX was syringed. An increase in viscosity was observed in 20 minutes. The solution was then stirred for overnight at reflux under nitrogen.

The polymer was precipitated into a large quantity of methanol, filtered and vacuum dried overnight.

This polymerization was also carried out in HFX and the same results were obtained.

Comparative Example 2

Preparation of Copolymer Containing Zonyl TA-N 1H, 1H, 2H, 2H-Perfluoroalkyl acrylate (Zonyl TA-N) (20.3 g, 0.0358 mol) and n-lauryl acrylate (6.85 g, 0.0285 mol) were charged into a 100 ml, 3 necked flask equipped same as that in example 5. 30 ml of HFX was added with a syringe. The solution was bubbled with nitrogen for 10 minutes. The flask was heated to 100° C. after AIBN in 2 ml of HFX was added with a syringe. An increase in viscosity was observed in 10 minutes. The solution was then stirred at 100° C. under nitrogen overnight.

Polymer was precipitated into a large quantity of methanol, filtered and vacuum dried overnight.

EXAMPLE 7

Coating Comparison Study

All samples were prepared under the same conditions except coating solvent because there is no common solvent for all studied polymers. Nylon-66 woven fabric was used as coating substrate. The fabric samples were soaked in methanol for 30 minutes, rinsed with methanol and air dried for one hour prior to coating. After dip-in coating, samples were first air dried for 20 minutes and then oven dried at 170° C. for 10 minutes. Each sample is described as follows:

Comparison Sample 1: 10"×10" sample was treated with 3 weight % of the polymer from Comparative Example 2 in HFX.

Comparison Sample 2: 10"×10" sample was treated with 3 weight % of the polymer from Comparative Example 2 in PF-5070 which is a fluorinated solvent obtained from 3M Corp.

Invention Sample 3: 10"×10" sample was treated with 3 weight % of the polymer from Example 5 in THF.

Invention Sample 4: 10"×10" sample was treated with 3 weight % of the polymer from Example 6 in THF.

Simulated laundering washings were done using a Parr shaker (hydrogenator). The shaking bottle contains water (300 ml) and Tide concentrated liquid soap (18 ml). Each sample was immersed in the soap solution in the bottle and the bottle shook for 24 hours at 40° C. Each sample was washed under the same conditions, and then rinsed with warm water under the same condition.

The specimens for DCA measurements were cut into 1.5 cm×1.5 cm sizes. Two such specimens were taken from each fabric sample at different locations. The DCA results for each sample were the average values from the two specimens.

Four DCA data were obtained for each sample at room temperature: (1) before washing; (2) after washing, rinse and air dried for overnight; (3) after washing, rinse, air dried for overnight and then oven dried at 60° C. for 30 minutes; (4) after washing, rinse, air dried for overnight; oven dried at 60° C. for 30 minutes and then oven dried at 170° C. for 20 minutes. The water receding contact angles are summarized in Table 1.

Table 1: Water Receding Contact Angles Under Different Conditions

|  |  | SAMPLE | | | |
| --- | --- | --- | --- | --- | --- |
|  |  | 1 | 2 | 3 | 4 |
| Initial (Before Washing) | | 65.7 | 115 | 113 | 173 |
| After | Air Dried | 19.4 | 52.5 | 79.0 | 81.7 |
| 24 hr. | 60° C. dried | 32.1 | 56.0 | 90.6 | 91.7 |
| Wash | 170° C. dried | 84.0 | 91.5 | 130 | 118 |

Table 1 shows that the polymers of the invention, in which the quite unique polymeric side chains are highly stabilized. This system offers very low and stable surface free energy which can be used as water/oil repellent coating materials. Compared with polymers based on 1H, 1H, 2H, 2H-perfluoroalkyl acrylate which (Comparisons 1 and 2) are systems for water repellent coatings, the inventive system is superior in terms of water repellency. The higher the water receding contact angle, the better the water repellency. Invention samples (Sample 3 and 4) have much higher water repellency and laundering durability than copolymer and homopolymer of 1H, 1H, 2H, 2H-perfluoroalkyl acrylate treated samples.

EXAMPLE 8

Treating Papers

Copolymer of Example 6 (0.4 g) was dissolved in THF (200 ml) by warming to make a solution. Xerox copy papers (25-8"×11") were treated with the solution by dipping for a few seconds. The treated papers were then air dried for 15 minutes and then dried in an oven for 20 minutes at 100° C.

The treated papers showed enhanced hydrophobicity and oleophobicity, while other properties remain unchanged. Table 2 summarizes hydrophobicity and oleophobicity of treated and untreated papers and Table 3 summarizes other properties.

TABLE 2

Hydrophobicity and Oleophobicity of Treated and Untreated Papers

| Test | Treated | Untreated |
|---|---|---|
| Oil Repellency (QCTM602) | 8 | 0 |
| Water Drop Repellency (QCTM604) | 5 | 4 |
| Impact Penetration (AATCC42) (g) | 0.03 | 0.06 |
| Water Absorptiveness (TAPPI441) (g/m$_2$) | 19.9 | 29.5 |
| Hydrostatic Pressure (AATCC127) | 70.5 cm | 47.2 cm |
| Spray Test (QCTM601) | 80 | 50 |

TABLE 3

Some Properties of Treated and Untreated Papers

| TEST | STAT | | Control | Treated |
|---|---|---|---|---|
| Weight (Grammage) | Mean | | 77.815 | 78.047 |
| (g/m$^2$) | Std Dev | | 0.613 | 1.232 |
| TAPPI 410 | | | | |
| n = 10 | | | | |
| Thickness | Mean | | 0.00388 | 0.00402 |
| (inches) | Std Dev | | 0.00012 | 0.00010 |
| TAPPI 411 | | | | |
| n = 10 | | | | |
| Air Permeability | Mean | | 14.7 | 15.2 |
| Gurley Method | Std Dev | | 2.1 | 2.2 |
| (sec/100 cc) | | | | |
| TAPPI 460 n = 10 | | | | |
| Burst Strength | Mean | | 34.3 | 31.6 |
| (psi) | Std Dev | | 2.1 | 2.4 |
| TAPPI 403 | | | | |
| n = 20 | | | | |
| Upright MVTR - B | Mean | | 855 | 840 |
| (g/m$^2$/24 hr) | Std Dev | | 11.6 | 19.5 |
| ASTM E96 | % CV | | 1.4 | 2.3 |
| n = 10 | | | | |
| Flexural Properties | | | | |
| TAPPI 451 | Mach | Mean | 227.9 | 230.7 |
| n = 10 m, 10 t | | Std Dev | 3.8 | 4.2 |
| Length (mm) | Trans | Mean | 136.5 | 138.0 |
| | | Std Dev | 3.4 | 1.2 |
| Flexing | Mach | Mean | 92,108 | 95,829 |
| Resistance | | Std Dev | 0.43 | 0.58 |
| (mm$^3$ g/m$^2$) | Trans | Mean | 19,791 | 20,511 |
| | | Std Dev | 0.31 | 0.01 |
| Handling | Mach | Mean | 118,368 | 122,784 |
| Stiffness | | Std Dev | 0.55 | 0.74 |
| (mm$^3$) | Trans | Mean | 25,433 | 26,281 |
| | | Std Dev | 0.39 | 0.12 |
| Elmendorf | Mach | Mean | 64 | 67 |
| Tear* (gf/ply) | | Std Dev | 0 | 6 |
| TAPPI 414 | Trans | Mean | 61 | 59 |
| n = 3 m, 3 t | | Std Dev | 5 | 2 |
| Tensile Properties | | | | |
| TAPPI 494 | Mach | Mean | 25.94 | 23.06 |
| Load @ | | Std Dev | 1.03 | 1.29 |
| Break (lbs) | Trans | Mean | 13.02 | 12.15 |
| | | Std Dev | 0.43 | 0.38 |
| Breaking | Mach | Mean | 25.94 | 23.06 |
| Force (lbs/in) | | Std Dev | 1.03 | 1.29 |
| | Trans | Mean | 13.02 | 12.15 |
| | | Std Dev | 0.43 | 0.38 |
| Displ @ | Mach | Mean | 0.1480 | 0.1334 |
| Break (inches) | | Std Dev | 0.0103 | 0.0136 |
| | Trans | Mean | 0.3417 | 0.3218 |
| | | Std Dev | 0.0201 | 0.0317 |
| % Elong @ | Mach | Mean | 2.084 | 1.879 |
| Break (%) | | Std Dev | 0.145 | 0.191 |

TABLE 3-continued

Some Properties of Treated and Untreated Papers

| TEST | STAT | | Control | Treated |
|---|---|---|---|---|
| | Trans | Mean | 4.813 | 4.532 |
| | | Std Dev | 0.282 | 0.447 |
| Tensile | Mach | Mean | 0.3337 | 0.2389 |
| Energy | | Std Dev | 0.0317 | 0.400 |
| Absorption | Trans | Mean | 0.4657 | 0.4002 |
| (in-lb/in$^2$) | | Std Dev | 0.0361 | 0.0593 |
| Surface Wettability | | | | |
| TAPPI 458 n = 10 | | Mean | | |
| Initial Contact | | Std Dev | | |
| Angle (°) | | | | |
| Rate of Wett- | | Mean | | |
| ability (°/sec) | | Std Dev | | |

EXAMPLE 9

Treating Orthopedic Cast Padding

Copolymer of Example 6 (5.0 g) was dissolved in THF (500 ml) by warming to make a solution. Several rolls of polyester cast padding were dipped into the solution for 20 seconds and then taken out and the excess solution was allowed to drip until dry. The paddings were then heated in an oven at 100° C. for 15 minutes. The treated paddings had an oil rating of 6. Their fibers were highly water repellent. Because of the open structure of padding, water may be forced into the treated padding and pseudo-wet it. However, the water is not retained and drips out quickly. In another test, a treated padding was placed on the surface of distilled water and no wetting was observed. The same padding was then placed on the surface of soap water (5 wt. % of liquid Tide) and it was wetted. The wetted padding was then rinsed with distilled water several times and shaken five times. This padding was again put on the surface of distilled water and no wetting was observed.

We claim:

1. A polymer comprising recurring units of a monomer of the formula

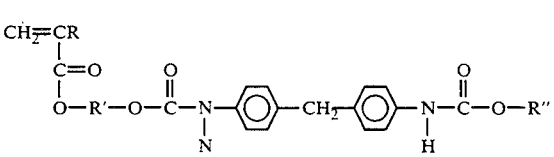

wherein:

R is H or —CH$_3$;

R' is alkyl of 2–8 carbon atoms; and

R" is fluorinated alkyl of 8–20 carbon atoms.

2. The polymer of claim 1 wherein R" is alkyl perfluoroalkyl of the formula —R—R$_1$ wherein R in —R—R$_1$ is alkyl of 1–2 carbon atoms and R$_1$ is perfluoroalkyl of 6–14 carbon atoms.

3. The polymer of claim 2 wherein R in —R—R$_1$ is —CH$_2$CH$_2$—.

4. A polymer of claim 1 wherein comonomer units are present which are units of an alkyl acrylate or methacrylate.

5. A polymer of claim 2 wherein comonomer units are present which are units of an alkyl acrylate or methacrylate.

6. A polymer of claim 3 wherein comonomer units are present which are units of an alkyl acrylate or methacrylate.

* * * * *